United States Patent
Guan et al.

(10) Patent No.: US 8,264,691 B2
(45) Date of Patent: *Sep. 11, 2012

(54) SURFACE PLASMON RESONANCE SPECTROMETER WITH AN ACTUATOR DRIVEN ANGLE SCANNING MECHANISM

(75) Inventors: Hann-Wen Guan, Bothwell, WA (US); Shuxin Cong, Lynnwood, WA (US)

(73) Assignee: Plexera, LLC, Woodinville, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/958,125

(22) Filed: Dec. 1, 2010

(65) Prior Publication Data

US 2011/0085167 A1    Apr. 14, 2011

Related U.S. Application Data

(63) Continuation of application No. 11/562,197, filed on Nov. 21, 2006, now Pat. No. 7,889,347.

(60) Provisional application No. 60/738,880, filed on Nov. 21, 2005.

(51) Int. Cl.
*G01J 4/00* (2006.01)

(52) U.S. Cl. ..................................... 356/445; 356/237.2

(58) Field of Classification Search .................... 356/445
See application file for complete search history.

(56) References Cited

U.S. PATENT DOCUMENTS

| | | | |
|---|---|---|---|
| 4,542,963 A * | 9/1985 | Linlor | 359/399 |
| 5,641,640 A * | 6/1997 | Hanning | 435/7.92 |
| 7,312,069 B2 * | 12/2007 | Ban et al. | 435/287.2 |
| 2005/0200845 A1 * | 9/2005 | Nabatova-Gabain et al. | 356/369 |
| 2007/0109542 A1 * | 5/2007 | Tracy et al. | 356/445 |

* cited by examiner

*Primary Examiner* — Gregory J Toatley
*Assistant Examiner* — Rebecca C Bryant
(74) *Attorney, Agent, or Firm* — Sci-Law Strategies, PC

(57) ABSTRACT

Instruments and methods relating to surface plasmon imaging are described. An instrument comprises a semi-circular rail and a driving mechanism. The driving mechanism is attached to a light source mount and a detector mount, and both the light source mount and the detector mount are attached to the semi-circular rail with connectors. Each connector allows the light source mount and detector mount to slide along the rail. The synchronous movement of the light source mount and the detector mount changes the angle of incidence of a light beam from the light source with respect to the plane of the sample surface on the sample stage.

18 Claims, 4 Drawing Sheets

SURFACE PLASMON RESONANCE SPECTROMETER WITH AN ACTUATOR DRIVEN ANGLE SCANNING MECHANISM

PRIORITY CLAIM

This application claims priority to U.S. patent application Ser. No. 11/562,197 filed Nov. 21, 2006 which claims priority to U.S. Provisional Patent Application Ser. No. 60/738,880, filed on Nov. 21, 2005, the entire contents of which are hereby incorporated by reference in their entireties.

TECHNICAL FIELD

This invention relates to scientific instruments and methods, and more particularly to surface plasmon resonance spectroscopy.

BACKGROUND

All patents, patent applications, and publications cited within this application are incorporated herein by reference to the same extent as if each individual patent, patent application or publication was specifically and individually incorporated by reference.

Surface Plasmon Resonance (SPR) spectroscopy is a powerful method capable of detecting molecular binding events at the nanometer scale by detecting changes in the effective refractive index or thickness of an adsorbed layer on or near an SPR active surface. When light is reflected from an SPR active medium at an angle greater than the critical angle, incident photons can generate surface plasmons. This phenomenon can be observed as a function of the reflected light intensity. The spatial difference of contrast can be acquired in an image format by employing a CCD camera as a detection system, namely SPR microscopy (SPRM).

Typically, SPR microscopy utilizes an angle of incidence of the irradiating beam at the prime SPR angle so that the system is conditioned to operate at its maximum linear response region. The procedure then involves rotating both sample and/or the detector and light source to establish the optimum optical pass configuration. Fine resolution rotation tables or linear diode arrays have been employed to provide the angular scanning function to obtain the SPR reflecting signal dip. Fixed wavelength, coherent angle scanning SPR employing dual rotation tables generally involves instruments having the optical pass configured in the horizontal plane. The physical size required for rotation stages offering fine resolution and providing enough torque to support the swing arms that hold either light source and/or detector gives the SPR instrument a large footprint. Thus, there is a need for an SPR instrument having a reduced footprint that allows SPR angle scanning.

SUMMARY

One embodiment is an SPR spectrometer comprising a semi-circular rail and a driving mechanism, wherein the driving mechanism is attached to a light source mount and a detector mount, and wherein both the light source mount and the detector mount are attached to the semi-circular rail with connectors, each connectors allowing the light source mount and detector mount to slide along the rail. Referring to FIG. 1, one embodiment is an instrument, comprising: a semicircular rail (2); a sample stage for receiving a sample (14), the sample stage forming a plane; a light source mount (8) on the rail (2); a light source (8a) on the light source mount (8); a detector mount (10) on the rail (2); a detector (10a) on the detector mount (10), wherein the light source mount (8) and the detector mount (10) move synchronously along the rail (2) in opposite directions (11a, 11b). The synchronous movement of the light source mount (8) and the detector mount (10) changes the angle of incidence of a light beam (12) from the light source (8a) with respect to the plane of the sample surface on the sample stage (14).

In another embodiment, the instrument further comprises a driving mechanism that comprises, referring to FIG. 2: a driving bridge (3) having a first pivot point (4a) and a second pivot point (6a); a first swing arm (4) with a first end (4b) and a second end (4c), the first end (4b) being connected to the driving bridge (3) through the first pivot point (4a); and a second swing arm (6) with a first end (6b) and a second end (6c), the first end (6b) being connected to the driving bridge (3) through the second pivot point (6a), wherein the second end (4c) of the first swing arm (4) is connected to a pivot point on the light source mount (8b) and the second end (6c) of the second swing arm (6) is connected to a pivot point on the detector mount (10b). Referring to FIGS. 2 and 3, when the driving bridge (3) moves along a path (15) substantially perpendicular to the plane of the sample stage, the light source mount (8) and the detector mount (10) move in opposite directions (11a and 11b). Using a single actuator to move the driving mechanism significantly reduces the instrument's physical size and mechanical complexity needed when, for example, dual rotation tables are used.

Another embodiment is a method, comprising: 1) providing a light source, a detector, and a sample, wherein the light source generates a light beam; 2) directing the light beam at the sample to form an angle of incidence between the light beam and the sample; and 3) moving the light source and the detector synchronously by sliding the light source and detector in opposite directions along a semicircular rail, thereby modifying the angle of incidence. In another embodiment, the sample is a microarray comprising gold and the light beam generates surface plasmon resonance at the gold surface.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
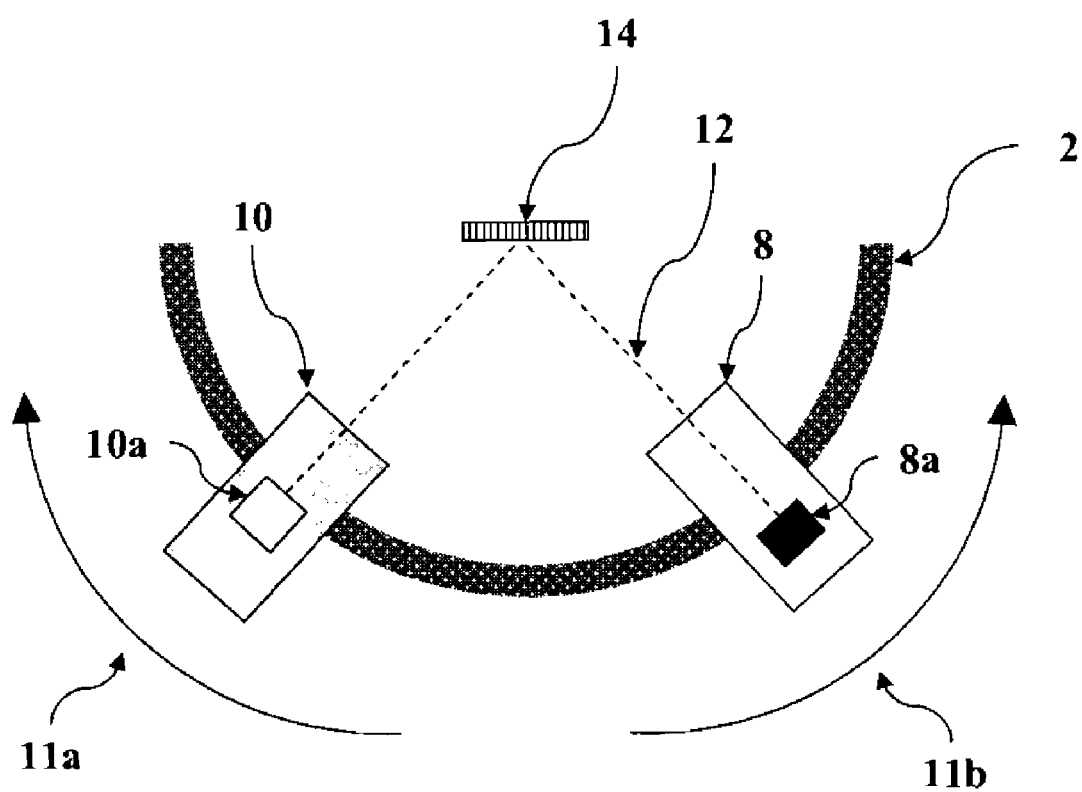
FIG. 1 illustrates one embodiment.

Referring to FIG. 1, one embodiment is an instrument, comprising: a semicircular rail (2); a sample stage for receiving a sample (14), the sample stage (14) forming a plane on which a sample may be placed; a light source mount (8) on the rail (2); a light source (8a) on the light source mount (8); a detector mount (10) on the rail (2); a detector (10a) on the detector mount (10), wherein the light source mount (8) and the detector mount (10) move synchronously along the rail (2) in opposite directions (denoted by arrows 11a and 11b). The synchronous movement of the light source mount (8) and the detector mount (10) changes the angle of incidence of a light beam (12) from the light source (8a) with respect to the plane of the sample surface on the sample stage (14). The sample stage (14) may be used for a microarray sample comprising gold, for example. The sample stage (14) may further include a microfluidic flow cell for supplying a liquid analyte to the surface of the microarray, and temperature regulator that may be used to influence instrument sensitivity by suppressing thermally induced sample changes in refractive index.

Figure 2:
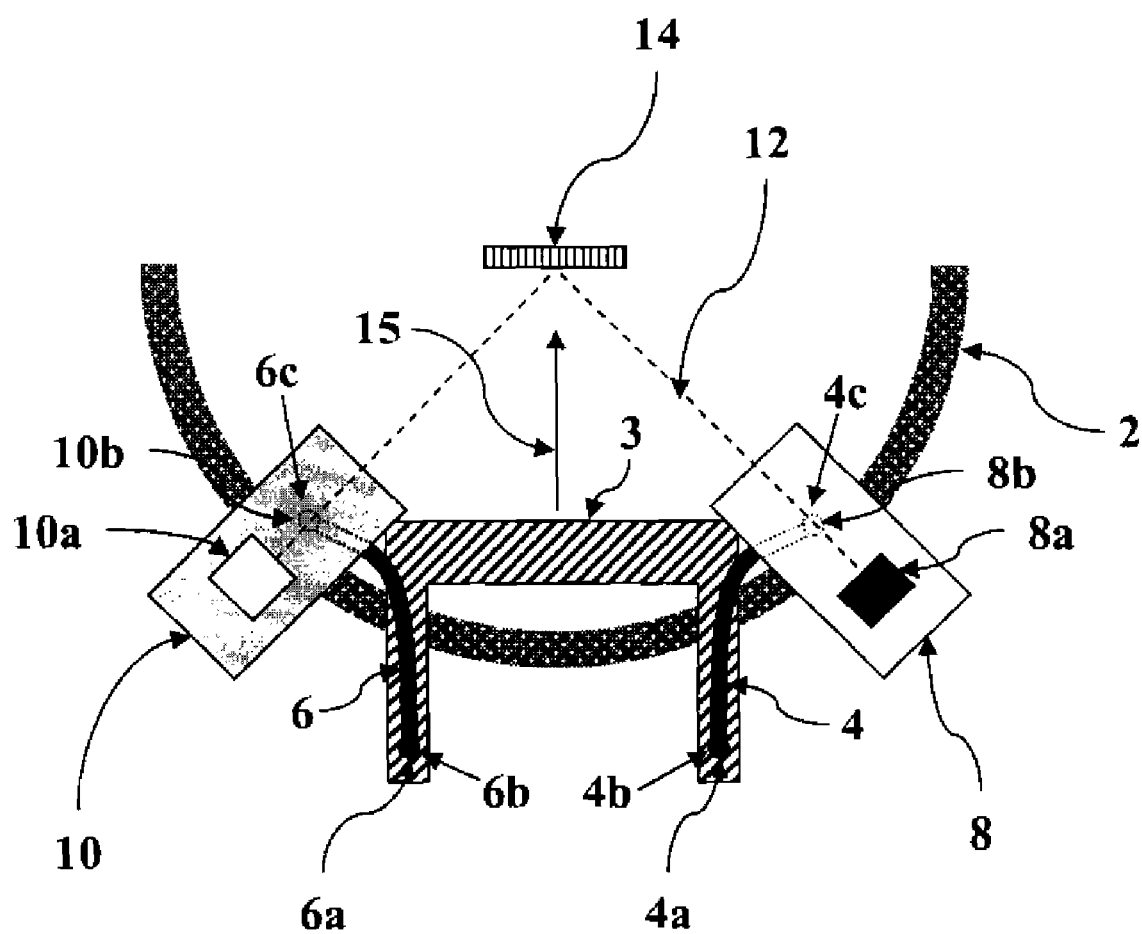
FIG. 2 illustrates another embodiment that includes a driving mechanism.
Figure 3:
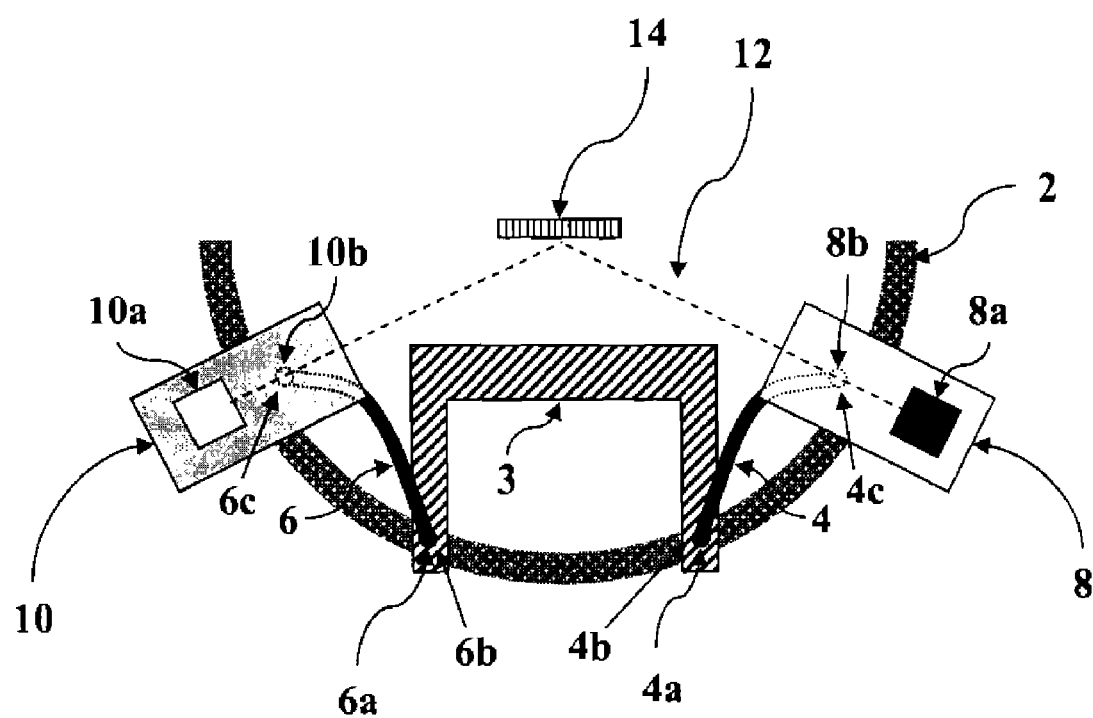
FIG. 3 illustrates the movement of some components in FIG. 2.

In another embodiment, the instrument further comprises a driving mechanism that comprises, referring to FIG. 2: a driving bridge (3) having a first pivot point (4a) and a second pivot point (6a); a first swing arm (4) with a first end (4b) and a second end (4c), the first end (4b) being connected to the driving bridge (3) through the first pivot point (4a); and a second swing arm (6) with a first end (6b) and a second end (6c), the first end (6b) being connected to the driving bridge (3) through the second pivot point (6a), wherein the second end (4c) of the first swing arm (4) is connected to a pivot point on the light source mount (8b) and the second end (6c) of the second swing arm (6) is connected to a pivot point on the detector mount (10b). Referring to FIGS. 2 and 3, when the driving bridge (3) moves along a path (15) substantially perpendicular to the plane of the sample stage (14), the light source mount (8) and the detector mount (10) move in opposite directions (denoted by arrows 11a and 11b in FIG. 1).

In one embodiment, the movement of the driving bridge (3) is effected by a linear actuator. In another embodiment, the light source (8a) comprises a laser that generates a laser beam. In many embodiments, the laser beam is scanned across the surface of the sample with a microelectromechanical (MEMS) scanner. The MEMS scanner can use a micromirror to reflect and manipulate the light beam path, for example see U.S. Pat. Nos. 6,245,590; 6,362,912; 6,433,907; and 5,629,790. In one embodiment the laser operates at wavelengths from about 360 nm to about 2000 nm. In many embodiments, the detector (10a) is a CCD camera. In other embodiments, the instrument further comprises a prism assembly mounted beneath the sample stage (14).

During operation in such a configuration, a prism in the prism assembly is located at the bottom of the sample. The prism assembly and the sample (e.g., a microarray substrate) are made of materials with similar refractive indices and are coupled to each other with an index-matching fluid. Light from the light source (8a) passes through one face of the prism, passes through the face of the prism that is coupled to the substrate of the microarray, and reflects off the sample surface (e.g., a gold surface). The reflected light again passes through the face of the prism coupled to the sample substrate, passes through a third face of the prism, and impinges on the detector (10a).

In most embodiments, the sample plane is roughly perpendicular to the plane of the semi-circular rail (2). The first swing arm (4) and the second swing arm (6) may be curved. The amount of curvature can depend on many factors including, for example, the distance between the sample (14) and the light source mount (8), the corresponding curvature of the rail (2), and the location of the pivot points (4b, 4c, 6b, and 6c). Each of the light source mount (8) and the detector mount (10) can rest, for example, on the semicircular rail (2) through at least two wheels. The light source mount (8) may further include a polarizer. In some embodiments, the instrument includes a mirror assembly. The mirror assembly can provide flexibility in placing the light source (8a) on the light source mount (8). In other embodiments, the detector mount (10) further includes a telescope in the light path (12) between the sample (14) and the detector (10a).

Another embodiment is a method, comprising: providing a light source, a detector, and a sample, wherein the light source generates a light beam; directing the light beam at the sample thereby forming an angle of incidence between the light beam and the sample; and moving the light source and the detector substantially synchronously by sliding the light source and detector in opposite directions along a semicircular rail, thereby modifying the angle of incidence. In one embodiment of the method, the sample is a microarray comprising gold and the light beam generates a surface plasmon at the gold surface. Methods and systems for producing microarrays on gold are well known. Microarrays of, for example, nucleic acids, peptides, or proteins covalently or noncovalently bound to a thiol monolayer can be produced on the surface of a gold substrate. The spots on the microarray may be separated from each other, for example, by hydrophobic areas in cases where the spots are hydrophilic. In many embodiments of the method, the detector is a CCD camera having pixels. One pixel may correspond, for example, to a single spot on the microarray to give a pixel-spot assignment, wherein the pixel-spot assignment does not change as the angle of incidence is modified. Alternatively, a group of pixels of the CCD camera may correspond to a single spot on the microarray, forming a pixel group-spot assignment, wherein the pixel group-spot assignment does not change as the angle of incidence is modified. In another embodiment of the method, at least one linear actuator controls the sliding of the light source and the detector along the semicircular rail.

In all embodiments, the light source can be a laser that forms a laser beam. In many embodiments, the light beam is scanned across the surface of the sample with a frequency. The light beam may be scanned, for example, by using a MEMS scanner as described above. When the light beam is scanned, the rate at which the light source and the detector slide along the rail may be, for example, slower than the frequency of the scan rate such that sample is scanned at least once before the angle of incidence is substantially modified. This means that the detector can be exposed to one or more full scans before the angle of incidence is modified. In many embodiments the light source can include a laser capable of producing light at different wavelengths, for example, from 360 nm to 2000 nm.

Figure 4:
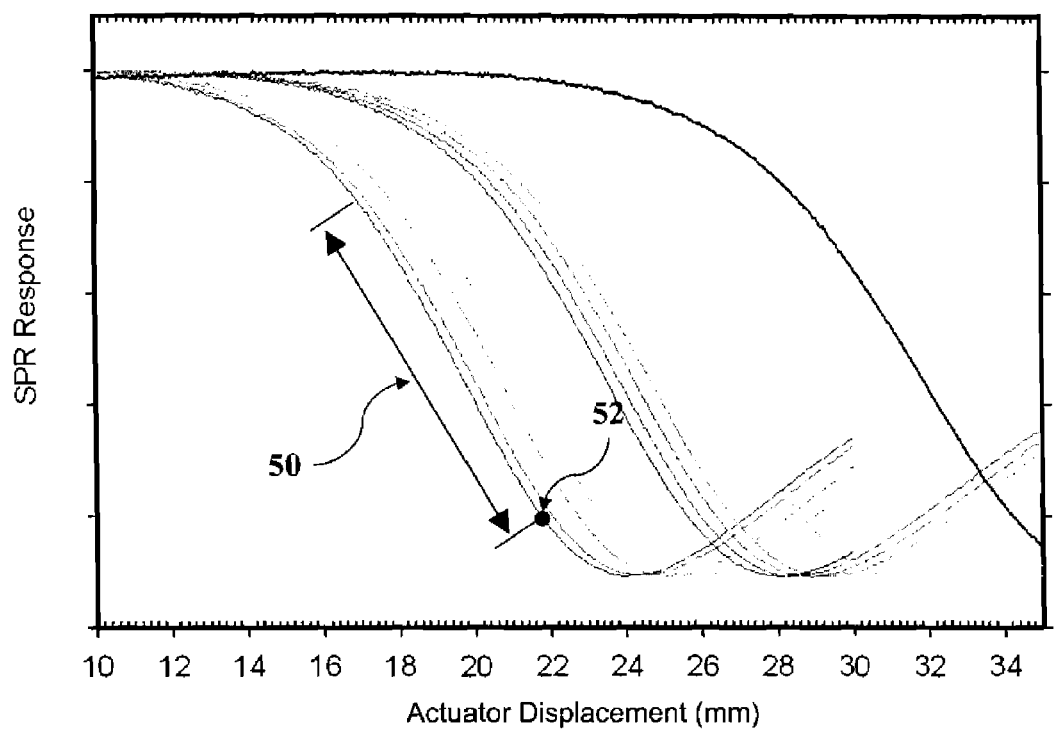
FIG. 4 is a plot of a surface plasmon resonance signal while modifying the angle of incidence.

In many embodiments, the light source is mounted on a light source mount; the detector is mounted on a detector mount; a first swing arm connects the light mount to a driving bridge; a second swing arm connects the detector mount to the driving bridge, and one linear actuator moves the driving bridge in a path perpendicular to a plane where the sample resides. In another embodiment, the method comprises: scanning a region on the microarray to be used in an assay; plotting the intensity of light at the detector against the magnitude of the displacement of the linear actuator to give a curve comprising a linear slope (50 in (FIG. 4)); choosing a specific point on the linear slope; moving the linear actuator to the displacement corresponding to the specific point to give a fixed angle of incidence; and performing the assay at the fixed angle of incidence. In many embodiments, referring to FIG. 4, the point is near the bottom of the linear slope (52).

A number of embodiments of the invention have been described. Nevertheless, it will be understood that various modifications may be made without departing from the spirit and scope of the invention. Accordingly, other embodiments are within the scope of the following claims.

What is claimed is:

1. A Surface Plasmon Resonance (SPR) spectrometer comprising:
    a semi-circular rail;
    a sample stage for receiving a sample, the sample stage forming a plane;
    a slidable light source associated with the rail;
    a mechanism to position the light source;
    a slidable detector associated with the rail;
    a driving bridge to link the movement of the slidable detector relative to the slidable light source;
    a mechanism for changing an incident angle of the light source and the position of the detector synchronously in opposite directions along the rail, wherein the intensity of the reflected light at the detector is measured at different positions of the light source and the detector to determine the optimum pass configuration; and
    a mechanism to adjust the position of the light source and the detector to an optimum pass configuration to measure a SPR spectrum.

2. The SPR spectrometer of claim 1, wherein optimizing the incident angle is used to determine the optimum pass configuration.

3. The SPR spectrometer of claim 1, further comprising a micromirror located at one or both the sample and the detector to manipulate the light beam path.

4. The SPR spectrometer of claim 1, further comprising a telescope tube located at the detector to reduce scattered light contributing to the detected light.

5. The SPR spectrometer of claim 1, wherein the detector is a CCD camera.

6. The SPR spectrometer of claim 1, wherein the light source is a light emitting diode.

7. The SPR spectrometer of claim 1, further comprising one or both one or more light polarizers and one or more wave plates positioned to alter the light emitted by the light source.

8. The SPR spectrometer of claim 1, further comprising a prism positioned to alter the light emitted by the light source.

9. The SPR spectrometer of claim 8, wherein optimizing the angle of incidence of the light entering the prism is used to determine the optimum pass configuration.

10. A method of measuring a Surface Plasmon Resonance (SPR) spectrum comprising:
    providing a sample comprising a microarray to be used in an assay, a light source associated with a semi-circular rail, a detector associated with the rail, and a driving bridge to link the movement of the detector relative to the light source, wherein the light source generates a light beam;
    positioning the light source;
    directing the light beam at the microarray to form an angle of incidence between the light beam and the microarray;
    determining an optimum pass configuration for the light source and the detector relative to the sample by moving the position of the light source and the detector synchronously in opposite directions along the rail, thereby modifying the angle of incidence and accumulating intensity of light at the detector at different positions of the light source and the detector; and
    accumulating the SPR spectrum for the optimum pass configuration.

11. The method of measuring a SPR spectrum of claim 10, wherein optimizing the incident angle is used to determine the optimum pass configuration.

12. The method of measuring a SPR spectrum of claim 10, further comprising a micromirror located at one or both the sample and the detector to manipulate the light beam path.

13. The method of measuring a SPR spectrum of claim 10, further comprising a telescope tube located at the detector to reduce scattered light contributing to the detected light.

14. The method of measuring a SPR spectrum of claim 10, wherein the detector is a CCD camera.

15. The method of measuring a SPR spectrum of claim 10, wherein the light source is a light emitting diode.

16. The method of measuring a SPR spectrum of claim 10, further comprising one or both one or more light polarizers and one or more wave plates positioned to alter the light emitted by the light source.

17. The method of measuring a SPR spectrum of claim 10, further comprising a prism positioned to alter the light emitted by the light source.

18. The method of measuring a SPR spectrum of claim 17, wherein optimizing the the angle of incidence of the light entering the prism is used to determine the optimum pass.

* * * * *